(12) United States Patent
Cabell et al.

(10) Patent No.: US 8,921,244 B2
(45) Date of Patent: Dec. 30, 2014

(54) HYDROXYL POLYMER FIBER FIBROUS STRUCTURES AND PROCESSES FOR MAKING SAME

(75) Inventors: David William Cabell, Cincinnati, OH (US); David Warren Loebker, Cincinnati, OH (US); Paul Dennis Trokhan, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 919 days.

(21) Appl. No.: 11/504,899

(22) Filed: Aug. 16, 2006

(65) Prior Publication Data

US 2007/0039704 A1    Feb. 22, 2007

Related U.S. Application Data

(60) Provisional application No. 60/710,109, filed on Aug. 22, 2005.

(51) Int. Cl.

| | |
|---|---|
| *D04H 3/00* | (2012.01) |
| *D04H 13/00* | (2006.01) |
| *D04H 1/54* | (2012.01) |
| *D04H 3/14* | (2012.01) |
| *D04H 5/06* | (2006.01) |
| *A61L 15/28* | (2006.01) |
| *D21H 13/08* | (2006.01) |
| *D06M 23/08* | (2006.01) |
| *D21H 17/67* | (2006.01) |

(52) U.S. Cl.
CPC ............ *D21H 13/08* (2013.01); *D21H 17/67* (2013.01); *A61L 15/28* (2013.01); *D06M 23/08* (2013.01)
USPC ............ 442/344; 442/340; 442/350; 442/409

(58) Field of Classification Search
USPC .................................. 442/340, 350, 409, 344
See application file for complete search history.

(56) References Cited

U.S. PATENT DOCUMENTS

| 2,008,031 | A | | 7/1931 | Miller | |
|---|---|---|---|---|---|
| 2,175,045 | A | | 10/1939 | Vogel | |
| 3,521,638 | A | * | 7/1970 | Parrish | ........................ 604/364 |
| 3,838,692 | A | * | 10/1974 | Levesque | ..................... 604/382 |

(Continued)

FOREIGN PATENT DOCUMENTS

| DE | 199 59 832 A1 | 7/2001 |
|---|---|---|
| EP | 0 080 382 A1 | 11/1982 |

(Continued)

OTHER PUBLICATIONS

Meyer et al., Comparison between different presentations of pore size distribution in porous materials. Fresenius J Anal Chem (1999) 363: 174-178.*

(Continued)

*Primary Examiner* — Jeremy R Pierce
(74) *Attorney, Agent, or Firm* — C. Brant Cook

(57) ABSTRACT

Hydroxyl polymer fiber fibrous structures and processes for making same are provided. More particularly, hydroxyl polymer fiber fibrous structures comprising a non-naturally occurring hydroxyl polymer fiber wherein the fibrous structure exhibits a total pore volume of pores in the range of greater than 20 μm to 500 μm of greater than 3.75 mm$^3$/mg of dry fibrous structure mass, and/or fibrous structures comprising a hydroxyl polymer fiber and a solid additive are provided.

18 Claims, 4 Drawing Sheets

(56) References Cited

U.S. PATENT DOCUMENTS

| | | | |
|---|---|---|---|
| 3,954,361 A | 5/1976 | Page | |
| 4,100,324 A | 7/1978 | Anderson et al. | |
| 4,118,531 A | 10/1978 | Hauser | |
| 4,139,699 A * | 2/1979 | Hernandez et al. | 536/109 |
| 4,203,939 A | 5/1980 | Drachenberg et al. | |
| 4,243,480 A * | 1/1981 | Hernandez et al. | 162/141 |
| 4,355,066 A | 10/1982 | Newman | |
| 4,370,289 A | 1/1983 | Sorenson | |
| 4,436,780 A | 3/1984 | Hotchkiss et al. | |
| 4,604,313 A | 8/1986 | McFarland et al. | |
| 4,623,576 A | 11/1986 | Lloyd et al. | |
| 4,634,621 A | 1/1987 | Manning et al. | |
| 4,636,418 A | 1/1987 | Kennard et al. | |
| 4,675,226 A | 6/1987 | Ott | |
| 4,720,415 A | 1/1988 | Vander Wielen et al. | |
| 4,724,114 A | 2/1988 | McFarland et al. | |
| 4,786,550 A | 11/1988 | McFarland et al. | |
| 4,803,117 A | 2/1989 | Daponte | |
| 4,851,168 A | 7/1989 | Graiver et al. | |
| 4,855,179 A | 8/1989 | Bourland et al. | |
| 4,863,779 A | 9/1989 | Daponte | |
| 4,879,170 A | 11/1989 | Radwanski et al. | |
| 4,885,202 A | 12/1989 | Lloyd et al. | |
| 4,906,513 A | 3/1990 | Kebbell et al. | |
| 4,931,355 A | 6/1990 | Radwanski et al. | |
| 4,939,016 A | 7/1990 | Radwanski et al. | |
| 4,970,104 A | 11/1990 | Radwanski | |
| 5,087,506 A * | 2/1992 | Palumbo | 442/394 |
| 5,094,717 A | 3/1992 | Manning et al. | |
| 5,120,888 A | 6/1992 | Nohr et al. | |
| 5,145,727 A | 9/1992 | Potts et al. | |
| 5,149,576 A | 9/1992 | Potts et al. | |
| 5,204,165 A | 4/1993 | Schortmann | |
| 5,227,107 A | 7/1993 | Dickenson et al. | |
| 5,254,133 A | 10/1993 | Seid | |
| 5,254,399 A | 10/1993 | Oku et al. | |
| 5,272,236 A | 12/1993 | Lai et al. | |
| 5,284,703 A | 2/1994 | Everhart et al. | |
| 5,350,624 A | 9/1994 | Georger et al. | |
| 5,375,306 A | 12/1994 | Roussin-Moynier | |
| 5,409,768 A | 4/1995 | Dickenson et al. | |
| 5,427,696 A | 6/1995 | Phan et al. | |
| 5,436,066 A * | 7/1995 | Chen | 442/398 |
| 5,476,616 A | 12/1995 | Schwarz | |
| 5,508,102 A | 4/1996 | Georger et al. | |
| 5,509,915 A * | 4/1996 | Hanson et al. | 604/378 |
| 5,536,563 A | 7/1996 | Shah et al. | |
| 5,539,056 A | 7/1996 | Yang et al. | |
| 5,587,225 A * | 12/1996 | Griesbach et al. | 442/408 |
| 5,597,873 A * | 1/1997 | Chambers et al. | 525/330.1 |
| 5,611,890 A | 3/1997 | Vinson et al. | |
| 5,629,080 A | 5/1997 | Gupta et al. | |
| 5,652,048 A | 7/1997 | Haynes et al. | |
| 5,811,178 A | 9/1998 | Adam et al. | |
| 5,814,570 A | 9/1998 | Cohen | |
| 5,853,867 A | 12/1998 | Harada et al. | |
| 5,948,710 A | 9/1999 | Pomplun et al. | |
| 5,952,251 A | 9/1999 | Jackson et al. | |
| 6,103,061 A | 8/2000 | Anderson et al. | |
| 6,150,005 A | 11/2000 | Williams et al. | |
| 6,172,276 B1 | 1/2001 | Hetzler et al. | |
| 6,177,370 B1 | 1/2001 | Skoog et al. | |
| 6,179,235 B1 | 1/2001 | King | |
| 6,200,120 B1 | 3/2001 | Fish et al. | |
| 6,261,679 B1 * | 7/2001 | Chen et al. | 428/317.9 |
| 6,296,936 B1 | 10/2001 | Yahiaoui et al. | |
| 6,319,342 B1 | 11/2001 | Riddell | |
| 6,348,133 B1 | 2/2002 | Woodrum | |
| 6,348,253 B1 | 2/2002 | Daley et al. | |
| 6,383,336 B1 | 5/2002 | Shannon | |
| 6,417,120 B1 | 7/2002 | Mitchler et al. | |
| 6,423,884 B1 * | 7/2002 | Oehmen | 604/369 |
| 6,465,073 B1 | 10/2002 | Morman et al. | |
| 6,488,801 B1 | 12/2002 | Bodaghi et al. | |
| 6,494,974 B2 | 12/2002 | Riddell | |
| 6,503,370 B2 * | 1/2003 | Hollmark et al. | 162/117 |
| 6,506,873 B1 | 1/2003 | Ryan et al. | |
| 6,550,115 B1 | 4/2003 | Skoog et al. | |
| 6,589,892 B1 | 7/2003 | Smith et al. | |
| 6,608,236 B1 | 8/2003 | Burns et al. | |
| 6,686,303 B1 | 2/2004 | Haynes et al. | |
| 6,709,526 B1 * | 3/2004 | Bailey et al. | 127/29 |
| 6,739,023 B2 | 5/2004 | Vonfeldt et al. | |
| 6,759,356 B1 | 7/2004 | Myers | |
| 6,797,226 B2 | 9/2004 | Annable | |
| 6,811,638 B2 | 11/2004 | Close et al. | |
| 6,823,568 B1 | 11/2004 | Kobayashi et al. | |
| 6,836,937 B1 | 1/2005 | Boscolo | |
| 6,946,413 B2 | 9/2005 | Lange et al. | |
| 6,979,386 B1 * | 12/2005 | Wallajapet et al. | 162/109 |
| 6,986,932 B2 | 1/2006 | Zink et al. | |
| 6,992,028 B2 | 1/2006 | Thomaschefsky et al. | |
| 7,000,000 B1 | 2/2006 | O'Brien | |
| 7,029,620 B2 | 4/2006 | Gordon et al. | |
| 7,176,150 B2 | 2/2007 | Kopacz et al. | |
| 7,208,429 B2 * | 4/2007 | Vinson et al. | 442/143 |
| 7,410,683 B2 | 8/2008 | Curro et al. | |
| 7,425,517 B2 | 9/2008 | Deka et al. | |
| 7,696,109 B2 | 4/2010 | Ouellette et al. | |
| 7,879,172 B2 | 2/2011 | Kopcz et al. | |
| 7,902,096 B2 | 3/2011 | Brandner et al. | |
| 7,972,986 B2 | 7/2011 | Barnholtz et al. | |
| 7,994,079 B2 | 8/2011 | Chen et al. | |
| 7,994,081 B2 | 8/2011 | Farrell et al. | |
| 7,998,889 B2 | 8/2011 | Stralin et al. | |
| 8,017,534 B2 | 9/2011 | Harvey et al. | |
| 2003/0024662 A1 | 2/2003 | Besemer et al. | |
| 2003/0073367 A1 | 4/2003 | Kopacz et al. | |
| 2003/0131457 A1 | 7/2003 | Krautkramer et al. | |
| 2003/0135172 A1 * | 7/2003 | Whitmore et al. | 604/359 |
| 2003/0150090 A1 | 8/2003 | Krautkramer et al. | |
| 2003/0200991 A1 | 10/2003 | Keck et al. | |
| 2003/0220039 A1 | 11/2003 | Chen et al. | |
| 2004/0048542 A1 | 3/2004 | Thomaschefsky et al. | |
| 2004/0065422 A1 | 4/2004 | Hu et al. | |
| 2004/0087237 A1 | 5/2004 | Garnier et al. | |
| 2004/0096656 A1 * | 5/2004 | Bond | 428/373 |
| 2004/0106723 A1 | 6/2004 | Yang et al. | |
| 2004/0163781 A1 | 8/2004 | Hernandez-Munoa et al. | |
| 2004/0181199 A1 | 9/2004 | Moberg-Alehammar et al. | |
| 2005/0020170 A1 | 1/2005 | Deka et al. | |
| 2005/0056956 A1 | 3/2005 | Zhao et al. | |
| 2005/0090175 A1 | 4/2005 | Bergholm et al. | |
| 2005/0103455 A1 | 5/2005 | Edwards et al. | |
| 2005/0112980 A1 | 5/2005 | Strandqvist et al. | |
| 2005/0130536 A1 | 6/2005 | Siebers et al. | |
| 2005/0130544 A1 | 6/2005 | Cheng et al. | |
| 2005/0133177 A1 | 6/2005 | Stralin et al. | |
| 2005/0136765 A1 | 6/2005 | Shannon | |
| 2005/0136772 A1 | 6/2005 | Chen et al. | |
| 2005/0136778 A1 | 6/2005 | Thomaschefsky et al. | |
| 2005/0148264 A1 | 7/2005 | Varona et al. | |
| 2005/0159065 A1 | 7/2005 | Stralin et al. | |
| 2005/0170727 A1 | 8/2005 | Melik et al. | |
| 2005/0177122 A1 | 8/2005 | Berba et al. | |
| 2005/0245159 A1 | 11/2005 | Chmielewski et al. | |
| 2005/0247416 A1 * | 11/2005 | Forry et al. | 162/109 |
| 2005/0274470 A1 | 12/2005 | Shannon et al. | |
| 2006/0088697 A1 | 4/2006 | Manifold et al. | |
| 2007/0010153 A1 | 1/2007 | Shaffer et al. | |
| 2007/0049153 A1 | 3/2007 | Dunbar et al. | |
| 2007/0063091 A1 | 3/2007 | Neveu | |
| 2007/0173162 A1 | 7/2007 | Ethiopia et al. | |
| 2007/0202766 A1 | 8/2007 | Ouellette et al. | |
| 2007/0232180 A1 | 10/2007 | Polat et al. | |
| 2007/0272381 A1 | 11/2007 | Elony et al. | |
| 2008/0000602 A1 | 1/2008 | Dyer et al. | |
| 2008/0008853 A1 | 1/2008 | Hupp et al. | |
| 2008/0041543 A1 | 2/2008 | Dyer et al. | |
| 2008/0050996 A1 | 2/2008 | Stralin et al. | |
| 2008/0051471 A1 | 2/2008 | Kronberg et al. | |
| 2008/0142178 A1 | 6/2008 | Haubrich et al. | |
| 2008/0248239 A1 | 10/2008 | Pomeroy et al. | |
| 2009/0022960 A1 | 1/2009 | Suer et al. | |

(56) References Cited

U.S. PATENT DOCUMENTS

| | | |
|---|---|---|
| 2009/0022983 A1 | 1/2009 | Cabell et al. |
| 2009/0023839 A1 | 1/2009 | Barnholtz et al. |
| 2009/0025894 A1 | 1/2009 | Barnholtz et al. |
| 2009/0084513 A1 | 4/2009 | Barnholtz et al. |
| 2009/0151748 A1 | 6/2009 | Ridenhour |
| 2009/0220741 A1 | 9/2009 | Manifold et al. |
| 2009/0220769 A1 | 9/2009 | Manifold et al. |
| 2010/0239825 A1 | 9/2010 | Sheehan et al. |
| 2010/0326612 A1 | 12/2010 | Hupp et al. |
| 2011/0100574 A1 | 5/2011 | Barnholtz et al. |
| 2011/0104419 A1 | 5/2011 | Barnholtz et al. |
| 2011/0104444 A1 | 5/2011 | Barnholtz et al. |
| 2011/0104493 A1 | 5/2011 | Barnholtz et al. |
| 2011/0104970 A1 | 5/2011 | Barnholtz et al. |
| 2011/0209840 A1 | 9/2011 | Barnholtz et al. |
| 2011/0220310 A1 | 9/2011 | Polat et al. |
| 2011/0244199 A1 | 10/2011 | Brennan et al. |

FOREIGN PATENT DOCUMENTS

| | | |
|---|---|---|
| EP | 0 156 649 A2 | 10/1985 |
| EP | 1 156 160 A2 | 10/1985 |
| EP | 0 294 137 A1 | 12/1988 |
| EP | 0 308 320 A2 | 3/1989 |
| EP | 0 333 209 B1 | 9/1989 |
| EP | 0 423 619 A1 | 4/1991 |
| EP | 0 205 242 B2 | 12/1991 |
| EP | 0 357 496 B1 | 5/1994 |
| EP | 0 590 307 B1 | 12/1998 |
| EP | 1 132 427 * | 9/2001 |
| EP | 1 132 427 A1 | 9/2001 |
| EP | 1 156 147 A1 | 11/2001 |
| EP | 1 887 036 A2 | 2/2008 |
| EP | 1 504 145 B1 | 11/2008 |
| EP | 2 028 296 A1 | 2/2009 |
| GB | 2113731 | 8/1983 |
| JP | 59-211667 A | 11/1984 |
| JP | 08-174735 A | 7/1996 |
| JP | 2000/303335 A2 | 10/2000 |
| JP | 2002/088660 A | 3/2002 |
| JP | 2004-141255 A | 5/2004 |
| JP | 2005/218525 A2 | 8/2005 |
| WO | WO 92/07985 A1 | 5/1992 |
| WO | WO 94/19179 A1 | 9/1994 |
| WO | WO 97/37757 A1 | 10/1997 |
| WO | WO 98/03713 A1 | 1/1998 |
| WO | WO 98/27257 A2 | 6/1998 |
| WO | WO 98/36117 A1 | 8/1998 |
| WO | WO 98/55295 A1 | 12/1998 |
| WO | WO 00/11998 A1 | 3/2000 |
| WO | WO 00/21476 * | 4/2000 |
| WO | WO 00/29655 A1 | 5/2000 |
| WO | WO 00/38565 A1 | 7/2000 |
| WO | WO 00/63486 A1 | 10/2000 |
| WO | WO 01/09023 A1 | 2/2001 |
| WO | WO 01/66345 A1 | 9/2001 |
| WO | WO 02/50357 A1 | 6/2002 |
| WO | WO 02/053003 A2 | 7/2002 |
| WO | WO 02/053365 A2 | 7/2002 |
| WO | WO 03/050347 A1 | 6/2003 |
| WO | WO 03/080905 A1 | 10/2003 |
| WO | WO 2004/092474 A2 | 10/2004 |
| WO | WO 2005/065516 A2 | 7/2005 |
| WO | WO 2005/065932 | 7/2005 |
| WO | WO 2005/073446 A1 | 8/2005 |
| WO | WO 2005/080497 A1 | 9/2005 |
| WO | WO 2005/106085 A1 | 11/2005 |
| WO | WO 2005/118934 A1 | 12/2005 |
| WO | WO 2006/027810 A1 | 3/2006 |
| WO | WO 2006/060816 A1 | 6/2006 |
| WO | WO 2006/069120 A2 | 6/2006 |
| WO | WO 2007/070064 A1 | 6/2007 |
| WO | WO 2007/070075 A1 | 6/2007 |
| WO | WO 2007/078344 A1 | 7/2007 |
| WO | WO 2007/092303 A2 | 8/2007 |
| WO | WO 2007/098449 A1 | 8/2007 |
| WO | WO 2007/100936 A2 | 9/2007 |
| WO | WO 2007/124866 A1 | 11/2007 |
| WO | WO 2007/135624 A2 | 11/2007 |
| WO | WO 2008/005500 A2 | 1/2008 |
| WO | WO 2008/050311 A2 | 5/2008 |
| WO | WO 2008/073101 A1 | 6/2008 |
| WO | WO 2009/010938 A1 | 1/2009 |
| WO | WO 2009/010939 A2 | 1/2009 |
| WO | WO 2009/010940 A2 | 1/2009 |
| WO | WO 2009/010941 A2 | 1/2009 |
| WO | WO 2009/010942 A2 | 1/2009 |
| WO | WO 2006/060813 A1 | 6/2009 |
| WO | WO 2006/060815 A2 | 6/2009 |
| WO | WO 2009/105490 A1 | 8/2009 |
| WO | WO 2011/019908 A1 | 2/2011 |
| WO | WO 2011/053677 A1 | 5/2011 |

OTHER PUBLICATIONS

International Search Report Dated Jul. 12, 2006.
Anonymous, "NanoDispense® Contact Angle Measurements", *First Ten Angstroms*, (Oct. 3, 2004). Retrieved from the Internet: URL: http://www.firsttenangstroms.com/pdfdocs/NanoDispenseExamples.pdf, (retrieved Feb. 15, 2011) Entire document.
Meyer, et al., "Comparison between different presentations of pore size distribution in porous materials." Fresenius J. Anal Chem. 1999. 363: pp. 174-178.
Office Action U.S. Appl. No. 12/170,565 Mailed Mar. 2, 2011 (P&G Case 10860).
Complete Textile Glossary, Celaneses Acetate (2001), definition of "filament".

* cited by examiner

US 8,921,244 B2

HYDROXYL POLYMER FIBER FIBROUS STRUCTURES AND PROCESSES FOR MAKING SAME

CROSS REFERENCE TO RELATED APPLICATIONS

This application claims the benefit of U.S. Provisional Application No. 60/710,109 filed on Aug. 22, 2005.

FIELD OF THE INVENTION

The present invention relates to hydroxyl polymer fiber fibrous structures and processes for making same. More particularly, the present invention relates to hydroxyl polymer fiber fibrous structures comprising a non-naturally occurring hydroxyl polymer fiber wherein the fibrous structure exhibits a total pore volume of pores in the range of greater than 20 μm to 500 μm of greater than 3.75 mm$^3$/mg dry fibrous structure mass, as determined by the Pore Volume Distribution Test Method, described herein, and/or fibrous structures comprising a hydroxyl polymer fiber and a solid additive.

BACKGROUND OF THE INVENTION

Hydroxyl polymer fiber fibrous structures are known in the art. However, such fibrous structures have a tendency to collapse (i.e., decrease in caliper in the z-direction, which is perpendicular to the planar surfaces of the fibrous structures) (and definitely not "grow"; i.e., increase in caliper in the z-direction) when subjected to a liquid, such as water.

Accordingly, there is a need for hydroxyl polymer fiber fibrous structures that avoid or reduce such a collapse when subjected to a liquid, and process for making same.

SUMMARY OF THE INVENTION

The present invention fulfills the need described above by providing hydroxyl polymer fiber fibrous structures that avoid or reduce collapse of the fibrous structure and/or that grow or have one or more portions that grow when the fibrous structure is subjected to a liquid, and processes for making same.

In one example of the present invention, a fibrous structure comprising a plurality of non-naturally occurring polysaccharide fibers and a plurality of solid additives, is provided. In one example, such a fibrous structure exhibits a total pore volume of pores in the range of greater than 20 μm to 500 μm of greater than 3.75 and/or greater than 3.81 and/or greater than 3.87 and/or greater than 3.90 and/or greater than 3.96 and/or greater than 4.00 mm$^3$/mg dry fibrous structure mass, as determined by the Pore Volume Distribution Test Method, described herein.

In another example of the present invention, a fibrous structure comprising a non-naturally occurring hydroxyl polymer fiber wherein the fibrous structure exhibits a total pore volume of pores in the range of greater than 20 μm to 500 μm of greater than 3.75 and/or greater than 3.81 and/or greater than 3.87 and/or greater than 3.90 and/or greater than 3.96 and/or greater than 4.00 mm$^3$/mg dry fibrous structure mass, as determined by the Pore Volume Distribution Test Method, described herein, is provided.

In another example of the present invention, a fibrous structure comprising a non-naturally occurring hydroxyl polymer fiber and a solid additive, is provided.

In still another example of the present invention, a single- or multi-ply sanitary tissue product comprising a fibrous structure according to the present invention is provided.

In yet another example of the present invention, a process for making a fibrous structure, the process comprising the steps of:
a. providing a fibrous structure comprising a plurality of non-naturally occurring hydroxyl polymer fibers; and
b. contacting a surface of the fibrous structure with a plurality of solid additives such that the solid additives cover less than the entire surface area of the surface of the fibrous structure, is provided.

In even yet another example of the present invention, a process for making a fibrous structure, the process comprising the steps of:
a. providing a first gas stream comprising a plurality of non-naturally occurring hydroxyl polymer fibers;
b. providing a second gas stream comprising a plurality of solid additives; and
c. collecting the non-naturally occurring hydroxyl polymer fibers and the solid additives on a collection device such that a fibrous structure is formed, is provided.

In still yet another example of the present invention, a fibrous structure comprising non-naturally occurring hydroxyl polymer fibers and solid additives, wherein the non-naturally occurring hydroxyl polymer fibers are present in the fibrous structure at a greater bone dry weight than the solid additives, is provided.

In even still another example of the present invention, a fibrous structure comprising a plurality of non-naturally occurring hydroxyl polymer fibers and a pore volume enhancing system that increases the total pore volume per dry fibrous structure mass of pores in the range of greater than 20 μm to 500 μm of the fibrous structure compared to the same fibrous structure without the pore volume enhancing system. In one example, the pore volume enhancing system may comprise a solid additive.

In even still yet another example of the present invention, a fibrous structure comprising a plurality of non-naturally occurring hydroxyl polymer fibers wherein at least a portion of the fibrous structure remains elevated above another portion of the fibrous structure after both portions have been subjected to a liquid, such as an aqueous liquid (for example water).

In still yet another example of the present invention, a fibrous structure comprising a plurality of non-naturally occurring hydroxyl polymer fibers wherein at least a portion of the fibrous structure exhibits a height after being subjected to a liquid, such as an aqueous liquid (for example water), that is greater than its height prior to being subjected to a liquid, such as an aqueous liquid (for example water).

Accordingly, the present invention provides fibrous structures comprising a non-naturally occurring hydroxyl polymer fiber wherein the fibrous structure exhibits a total pore volume of pores in the range of greater than 20 μm to 500 μm of greater than 3.75 mm$^3$/mg dry fibrous structure mass, as determined by the Pore Volume Distribution Test Method, described herein, fibrous structures comprising a non-naturally occurring hydroxyl polymer fiber and a solid additive, fibrous structures comprising a pore volume enhancing system, sanitary tissue products comprising such fibrous structures and processes for making such fibrous structures.

DETAILED DESCRIPTION OF THE INVENTION

Definitions

Figure 1A:
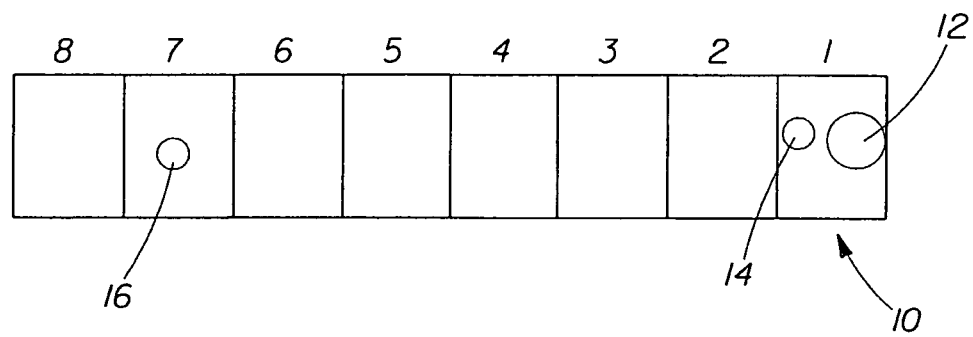
FIG. 1A is a schematic representation of a side view of a barrel of a twin screw extruder suitable for use in the present invention.

"Non-naturally occurring" as used herein with respect to "non-naturally occurring hydroxyl polymer fibers" and/or "non-naturally occurring materials" means that the hydroxyl polymer fibers and/or materials are not found in nature in that form. In other words, some chemical processing of materials needs to occur in order to obtain the non-naturally occurring hydroxyl polymer fibers and/or non-naturally occurring materials. For example, wood pulp fiber is a naturally occurring hydroxyl polymer fiber, however, if the wood pulp fiber is chemically processed, such as via a lyocell-type process, a solution of hydroxyl polymer is formed. The solution of hydroxyl polymer may then be spun into a fiber. Accordingly, this fiber is considered to be a non-naturally occurring hydroxyl polymer fiber since it is not directly obtainable from nature in its present form.

"Naturally occurring" as used herein means that a material is found in nature in its present form. An example of a naturally occurring material is a wood pulp fiber.

A "fibrous structure" as used herein means a single web structure that comprises at least one fiber. For example, a fibrous structure of the present invention may comprise one or more fibers, wherein at least one of the fibers comprises a hydroxyl polymer fiber. In another example, a fibrous structure of the present invention may comprise a plurality of fibers, wherein at least one (sometimes a majority, even all) of the fibers comprises a hydroxyl polymer fiber. The fibrous structures of the present invention may be layered such that one layer of the fibrous structure may comprise a different composition of fibers and/or materials from another layer of the same fibrous structure.

"Surface of a fibrous structure" as used herein means that portion of a fibrous structure that is exposed to the external environment. In other words, the surface of a fibrous structure is that portion of the fibrous structure that is not completely surrounded by other portions of the fibrous structure.

"Hydroxyl polymer" as used herein includes any hydroxyl-containing polymer that can be incorporated into a fibrous structure of the present invention, such as into a fibrous structure in the form of a fiber.

In one example, the hydroxyl polymer of the present invention includes greater than 10% and/or greater than 20% and/or greater than 25% by weight hydroxyl moieties.

Nonlimiting examples of hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose, cellulose derivatives such as cellulose ether and ester derivatives, cellulose copolymers, gums, arabinans, galactans, proteins and various other polysaccharides and mixtures thereof.

Classes of hydroxyl polymers are defined by the hydroxyl polymer backbone. For example polyvinyl alcohol and polyvinyl alcohol derivatives and polyvinyl alcohol copolymers are in the class of polyvinyl alcohol hydroxyl polymers whereas starch and starch derivatives are in the class of starch hydroxyl polymers.

The hydroxyl polymer may have a weight average molecular weight of from about 10,000 to about 40,000,000 g/mol. Higher and lower molecular weight hydroxyl polymers may be used in combination with hydroxyl polymers having the exemplified weight average molecular weight.

Well known modifications of hydroxyl polymer, such as natural starches, include chemical modifications and/or enzymatic modifications. For example, the natural starch can be acid-thinned, hydroxy-ethylated, hydroxy-propylated, and/or oxidized. In addition, the hydroxyl polymer may comprise dent corn starch hydroxyl polymer.

Polyvinyl alcohols herein can be grafted with other monomers to modify its properties. A wide range of monomers has been successfully grafted to polyvinyl alcohol. Nonlimiting examples of such monomers include vinyl acetate, styrene, acrylamide, acrylic acid, 2-hydroxyethyl methacrylate, acrylonitrile, 1,3-butadiene, methyl methacrylate, methacrylic acid, vinylidene chloride, vinyl chloride, vinyl amine and a variety of acrylate esters.

"Polysaccharides" as used herein means natural polysaccharides and polysaccharide derivatives or modified polysaccharides. Suitable polysaccharides include, but are not limited to, starches, starch derivatives, chitosan, chitosan derivatives, cellulose derivatives, gums, arabinans, galactans and mixtures thereof.

"Fiber" as used herein means a slender, thin, and highly flexible object having a major axis which is very long, compared to the fiber's two mutually-orthogonal axes that are perpendicular to the major axis. In one example, an aspect ratio of the major's axis length to an equivalent diameter of the fiber's cross-section perpendicular to the major axis is greater than 100/1, more specifically greater than 500/1, and still more specifically greater than 1000/1, and even more specifically, greater than 5000/1.

The fibers of the present invention may be continuous or substantially continuous. A fiber is continuous if it extends 100% of the MD length of the fibrous structure and/or fibrous structure and/or sanitary tissue product made therefrom. In one example, a fiber is substantially continuous if it extends greater than about 30% and/or greater than about 50% and/or greater than about 70% of the MD length of the fibrous structure and/or sanitary tissue product made therefrom. In another example, continuous or substantially continuous fiber in accordance with the present invention may exhibit a length of greater than 3.81 cm (1.5 inches).

The fiber can have a fiber diameter as determined by the Fiber Diameter Test Method described herein of less than about 50 microns and/or less than about 20 microns and/or less than about 10 microns and/or less than about 8 microns and/or less than about 6 microns.

The fibers may include melt spun fibers, dry spun fibers and/or spunbond fibers, staple fibers, hollow fibers, shaped fibers, such as multi-lobal fibers and multicomponent fibers, especially bicomponent fibers. The multicomponent fibers, especially bicomponent fibers, may be in a side-by-side, sheath-core, segmented pie, ribbon, islands-in-the-sea configuration, or any combination thereof. The sheath may be continuous or non-continuous around the core. The ratio of the weight of the sheath to the core can be from about 5:95 to about 95:5. The fibers of the present invention may have different geometries that include round, elliptical, star shaped, rectangular, trilobal and other various eccentricities.

"Sanitary tissue product" as used includes but is not limited to a wiping implement for post-urinary and post-bowel movement cleaning (toilet tissue), for otorhinolaryngological discharges (facial tissue), and multi-functional absorbent, cleaning uses (absorbent towels), wipes, feminine care products and diapers.

A sanitary tissue product of the present invention comprises at least one fibrous structure in accordance with the present invention. In one example, a fibrous structure and/or sanitary tissue product according to the present invention exhibits an initial total wet tensile of at least about 8 g/2.54 cm (8 g/in) and/or at least about 10 g/2.54 cm (10 g/in) and/or at least about 15 g/2.54 cm (15 g/in) and/or at least about 20 g/2.54 cm (20 g/in) and/or at least about 40 g/2.54 cm (40 g/in).

In another example, a fibrous structure and/or a sanitary tissue product of the present invention exhibits an initial total wet tensile, as measured by the Initial Total Wet Tensile Test Method described herein, of less than about 500 g/2.54 cm (500 g/in) and/or less than about 400 g/2.54 cm (400 g/in) and/or less than about 300 g/2.54 cm (300 g/in) and/or less than about 200 g/2.54 cm (200 g/in) and/or less than about 150 g/2.54 cm (150 g/in) and/or less than about 120 g/2.54 cm (120 g/in) and/or less than about 100 g/2.54 cm (100 g/in).

In yet another example, a fibrous structure and/or a sanitary tissue product of the present invention may exhibit an initial total wet tensile of from about 8 g/2.54 cm (8 g/in) to about 500 g/2.54 cm (500 g/in) and/or from about 40 g/2.54 cm (40 g/in) to about 500 g/2.54 cm (500 g/in) and/or from about 60 g/2.54 cm (60 g/in) to about 500 g/2.54 cm (500 g/in) and/or from about 65 g/2.54 cm (65 g/in) to about 450 g/2.54 cm (450 g/in) and/or from about 70 g/2.54 cm (70 g/in) to about 400 g/2.54 cm (400 g/in) and/or from about 75 g/2.54 cm (75 g/in) to about 400 g/2.54 cm (400 g/in) and/or from about 80 g/2.54 cm (80 g/in) to about 300 g/2.54 cm (300 g/in) and/or from about 80 g/2.54 cm (80 g/in) to about 200 g/2.54 cm (200 g/in) and/or from about 80 g/2.54 cm (80 g/in) to about 150 g/2.54 cm (150 g/in) and/or from about 80 g/2.54 cm (80 g/in) to about 120 g/2.54 cm (120 g/in) and/or from about 80 g/2.54 cm (80 g/in) to about 100 g/2.54 cm (100 g/in).

In one example, a fibrous structure and/or a sanitary tissue product according to the present invention exhibits a minimum total dry tensile of at least about 70 g/2.54 cm (70 g/in) and/or at least about 100 g/2.54 cm (100 g/in) and/or at least about 300 g/2.54 cm (300 g/in) and/or at least about 500 g/2.54 cm (500 g/in) and/or at least about 700 g/2.54 cm (700 g/in) and/or at least about 800 g/2.54 cm (800 g/in) and/or at least about 900 g/2.54 cm (900 g/in) and/or at least about 1000 g/2.54 cm (1000 g/in).

In another example, a fibrous structure and/or a sanitary tissue product according to the present invention exhibits a maximum total dry tensile of less than about 5000 g/2.54 cm (5000 g/in) and/or less than about 4000 g/2.54 cm (4000 g/in) and/or less than about 2000 g/2.54 cm (2000 g/in) and/or less than about 1700 g/2.54 cm (1700 g/in) and/or less than about 1500 g/2.54 cm (1500 g/in).

In even another example, a fibrous structure and/or a sanitary tissue product according to the present invention exhibits a wet lint score of less than about 25 and/or less than 20 and/or less than 15 and/or less than 10.

In yet another example, a sanitary tissue product according to the present invention exhibits a total dry tensile within a range of a minimum and maximum total dry tensile value as described above.

In still yet another example, a fibrous structure and/or a sanitary tissue product according to the present invention exhibits a Dry Lint Score of less than about 10 and/or less than about 8 and/or less than about 7 and/or less than about 6 and/or less than about 5.5.

In addition to sanitary tissue products, the fibrous structures of the present invention may be utilized in any number of various other applications known in the art. For example, in some examples, the fibrous structures may be utilized as packaging materials, wound dressings, etc.

"Ply" or "Plies" as used herein means a single fibrous structure optionally to be disposed in a substantially contiguous, face-to-face relationship with other plies, forming a multi-ply sanitary tissue product. It is also contemplated that a single fibrous structure can effectively form two "plies" or multiple "plies", for example, by being folded on itself. Ply or plies can also exist as films.

One or more layers may be present in a single ply. For example, two or more layers of different compositions may form a single ply. In other words, the two or more layers are substantially or completely incapable of being physically separated from each other without substantially damaging the ply.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Caliper" as used herein means the macroscopic thickness of a sample. Caliper of a sample of fibrous structure according to the present invention is determined by cutting a sample of the fibrous structure such that it is larger in size than a load foot loading surface where the load foot loading surface has a circular surface area of about 3.14 in$^2$. The sample is confined between a horizontal flat surface and the load foot loading surface. The load foot loading surface applies a confining pressure to the sample of 15.5 g/cm$^2$ (about 0.21 psi). The caliper is the resulting gap between the flat surface and the load foot loading surface. Such measurements can be obtained on a VIR Electronic Thickness Tester Model II available from Thwing-Albert Instrument Company, Philadelphia, Pa. The caliper measurement is repeated and recorded at least five (5) times so that an average caliper can be calculated.

"Additive" as used herein means a material that is present in and/or on a fibrous structure at low levels. For example, an additive is a material that is present in and/or on a fibrous structure at levels less than 50% and/or less than 45% and/or less than 40% and/or less than 30% and/or less than 20% and/or less than 10% and/or less than 5% and/or less than 3% and/or less than 1% and/or less than 0.5% to about 0% by weight of the fibrous structure.

"Solid additive" as used herein means an additive that is capable of being applied to a surface of a fibrous structure in a solid form. In other words, the solid additive of the present invention can be delivered directly to a surface of a fibrous structure without a liquid phase being present, i.e. without melting the solid additive and without suspending the solid additive in a liquid vehicle or carrier. As such, the solid additive of the present invention does not require a liquid state or a liquid vehicle or carrier in order to be delivered to a surface of a fibrous structure. The solid additive or the present invention may be delivered via a gas or combinations of gases. For purposes of the present invention, delivery of an additive, liquid and/or solid, into a slurry of fibers used to produce a fibrous structure is not encompassed by this phrase. However, such an additive may be present in a finished fibrous structure so long as the finished fibrous structure also comprises a solid additive as defined herein. Further, an additive, liquid and/or solid, delivered to a fibrous structure via a liquid vehicle, such as a latex emulsion, may be present in a finished fibrous structure so long as the finished fibrous structure also comprises a solid additive as defined herein. Further, an additive, liquid and/or solid, delivered to a fibrous structure via melting, such as a hot melt adhesive, may be present in a finished fibrous structure so long as the finished fibrous structure also comprises a solid additive as defined herein. In one example, in simplistic terms, a solid additive is an additive that when placed within a container, does not take the shape of the container.

Nonlimiting examples of suitable solid additives include hydrophilic inorganic particles, hydrophilic organic particles, hydrophobic inorganic particles, hydrophobic organic particles, naturally occurring fibers, non-naturally occurring particles and other non-naturally occurring fibers.

In one example, the naturally occurring fibers may comprise wood pulp fibers, trichomes, seed hairs, protein fibers, such as silk and/or wool, and/or a cotton linters.

In another example, the other non-naturally occurring fibers may comprise polyolefin fibers and/or polyamide fibers.

In another example, the hydrophilic inorganic particles are selected from the group consisting of: clay, calcium carbonate, titanium dioxide, talc, aluminum silicate, calcium silicate, alumina trihydrate, activated carbon, calcium sulfate, glass microspheres, diatomaceous earth and mixtures thereof.

In one example, hydrophilic organic particles of the present invention may include hydrophobic particles the surfaces of which have been treated by a hydrophilic material. A description of a suitable process for surface treating a hydrophobic material with a hydrophilic material is described in U.S. Pat. No. 4,139,660. Nonlimiting examples of such hydrophilic organic particles include polyesters, such as polyethylene terephthalate particles that have been surface treated with a soil release polymer and/or surfactant. Another example is a polyolefin particle that has been surface treated with a surfactant.

In another example, the hydrophilic organic particles may comprise absorbent gel materials (AGM) such as hydrogels, superabsorbent materials, hydrocolloidal materials and mixtures thereof. In one example, the hydrophilic organic particle comprises polyacrylate. Other nonlimiting examples of suitable hydrophilic organic particles are known in the art. For example, U.S. Pat. No. 5,428,076 describes numerous examples of hydrophilic organic particles that are suitable for the present invention.

In another example, the hydrophilic organic particles may comprise high molecular weight starch particles (high amylose-containing starch particles), such as Hylon 7 available from National Starch.

In another example, the hydrophilic organic particles may comprises cellulose particles.

In another example, the hydrophilic organic particles may comprise compressed cellulose sponge particles. Fibrous structures comprising compressed cellulose sponge particles may expand more than 2 times and/or more than 3 times and/or more than 4 times their original state after being contacted by a liquid, such as an aqueous liquid (for example water).

In one example of a solid additive in accordance with the present invention, the solid additive exhibits a surface tension of greater than about 30 and/or greater than about 35 and/or greater than about 40 and/or greater than about 50 and/or greater than about 60 dynes/cm as determined by ASTM D2578.

The solid additives of the present invention may have different geometries and/or cross-sectional areas that include round, elliptical, star-shaped, rectangular, trilobal and other various eccentricities.

In one example, the solid additive may exhibit a particle size of less than 6 mm and/or less than 5.5 mm and/or less than 5 mm and/or less than 4.5 mm and/or less than 4 mm and/or less than 2 mm in its maximum dimension.

"Particle" as used herein means an object having an aspect ratio of less than about 25/1 and/or less than about 15/1 and/or less than about 10/1 and/or less than about 5/1 to about 1/1. A particle is not a fiber as defined herein.

Hydroxyl Polymer Fiber

The hydroxyl polymer fiber of the present invention may comprise one or more polymers. In one example, the hydroxyl polymer fiber comprises a first polymer and a second polymer, wherein one of the two polymers is inherently thermoplastic and thus, melts and/or flows without the need of a plasticizer when subjected to a temperature above its Tg. The other polymer may require a plasticizer, such as water, sorbitol, glycerine, polyols, such as polyethylene glycols, ethylene glycol, polyethylene glycol, urea, sucrose, and esters, and combinations thereof to permit it to melt and/or flow when subjected to a temperature above its Tg (i.e., a thermoplasticizable polymer). In one example, the first polymer and the second polymer are hydroxyl polymers. In another example, the first polymer and the second polymer are different classes of hydroxyl polymers, such as starch hydroxyl polymer and polyvinyl alcohol hydroxyl polymer. The polymers of the hydroxyl polymer fiber may be crosslinkable via a crosslinking system to themselves and/or to the each other.

The hydroxyl polymer fiber of the present invention can be produced by polymer processing, for example meltblowing, spunbonding, and/or rotary spinning, a polymer composition.

Polymer Composition

The polymer composition of the present invention may have a shear viscosity of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The polymer composition may have a temperature of from about 50° C. to about 100° C. and/or from about 65° C. to about 95° C. and/or from about 70° C. to about 90° C. when making fibers from the polymer composition.

The pH of the polymer composition may be from about 2.5 to about 9 and/or from about 3 to about 8.5 and/or from about 3.2 to about 8 and/or from about 3.2 to about 7.5.

In one example, a polymer composition of the present invention may comprise from about 30% and/or 40% and/or 45% and/or 50% to about 75% and/or 80% and/or 85% and/or 90% and/or 95% and/or 99.5% by weight of the polymer composition of a hydroxyl polymer. The hydroxyl polymer may have a weight average molecular weight greater than about 100,000 g/mol prior to crosslinking.

The polymer composition may exhibit a Capillary Number of at least 1 and/or at least 3 and/or at least 5 such that the polymer composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
η is the fluid viscosity at the conditions of the die (units of Mass per Length*Time),
σ is the surface tension of the fluid (units of mass per Time$^2$).

When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In a fiber spinning process, the filaments need to have initial stability as they leave the die. The Capillary number is used to characterize this initial stability criterion. At the conditions of the die, the Capillary number should be greater than 1 and/or greater than 4.

In one example, the polymer composition exhibits a Capillary Number of from at least 1 to about 50 and/or at least 3 to about 50 and/or at least 5 to about 30. Further, the polymer composition may exhibit a pH of from at least about 4 to about 12 and/or from at least about 4.5 to about 11.5 and/or from at least about 4.5 to about 11.

A crosslinking system comprising a crosslinking agent may be present in the polymer composition and/or may be added to the polymer composition before polymer processing of the polymer composition. Further, a crosslinking system may be added to the hydroxyl polymer fiber after polymer processing the polymer composition. "Crosslinking agent" as used herein means any material that is capable of crosslinking a hydroxyl polymer within a polymer composition according to the present.

Nonlimiting examples of suitable crosslinking agents include polycarboxylic acids, imidazolidinones and other compounds resulting from alkyl substituted or unsubstituted cyclic adducts of glyoxal with ureas, thioureas, guanidines, methylene diamides, and methylene dicarbamates and derivatives thereof; and mixtures thereof.

Upon crosslinking the hydroxyl polymer, the crosslinking agent becomes an integral part of the hydroxyl polymer fiber as a result of crosslinking the hydroxyl polymer as shown in the following schematic representation:

Hydroxyl polymer—Crosslinking agent—Hydroxyl polymer

In another example, the crosslinking system of the present invention may be applied to a pre-existing hydroxyl polymer fiber as a coating and/or surface treatment.

The polymer composition may comprise a) from about 30% and/or 40% and/or 45% and/or 50% to about 75% and/or 80% and/or 85% and/or 90% and/or 99.5% by weight of the polymer composition of one or more hydroxyl polymers; b) a crosslinking system comprising from about 0.1% to about 10% by weight of the polymer composition of a crosslinking agent; and c) from about 0% and/or 10% and/or 15% and/or 20% to about 50% and/or 55% and/or 60% and/or 70% by weight of the polymer composition of an external plasticizer e.g., water.

The polymer composition may comprise two or more different classes of hydroxyl polymers at weight ratios of from about 20:1 and/or from about 15:1 and/or from about 10:1 and/or from about 5:1 and/or from about 2:1 and/or from about 1:1 to about 1:20 and/or to about 1:15 and/or to about 1:10 and/or to about 1:5 and/or to about 1:2 and/or to about 1:1.

In one example, the polymer composition comprises from about 0.01% to about 20% and/or from about 0.1% to about 15% and/or from about 1% to about 12% and/or from about 2% to about 10% by weight of a first class of hydroxyl polymer, such as a polyvinyl alcohol hydroxyl polymer and from about 20% to about 99.99% and/or from about 25% to about 95% and/or from about 30% to about 90% and/or from about 40% to about 70% by weight of a second class of hydroxyl polymer, such as a starch hydroxyl polymer.

Process for Making a Hydroxyl Polymer Fiber Fibrous Structure

Any suitable process known to those skilled in the art can be used to produce the polymer composition and/or to polymer process the polymer composition and/or to produce the hydroxyl polymer fiber of the present invention. Nonlimiting examples of such processes are described in published applications: EP 1 035 239, EP 1 132 427, EP 1 217 106, EP 1 217 107, WO 03/066942 and U.S. Pat. No. 5,342,225.

a. Making a Polymer Composition

In one example, a polymer. composition according to the present invention, comprises a first class of polymers and a second class of polymers. The first class of polymers, which in this example comprises about 50:50 dry weight ratio of two different starches, comprises an acid thinned dent corn starch hydroxyl polymer (for example Eclipse® G—commercially available from A. E. Staley) and an ethoxylated corn starch hydroxyl polymer (for example Ethylex® 2035—commercially available from A. E. Staley) and the second class of polymers comprises a polyvinyl alcohol hydroxyl polymer (for example Celvol® 310—commercially available from Celanese). In addition to the hydroxyl polymers, the polymer composition comprises an alkaline agent, (for example sodium hydroxide), a cationic agent (for example Arquad® 12-37—commercially available from Akzo Nobel), a crosslinking system comprising a crosslinking agent as described herein, and a crosslinking facilitator (for example ammonium chloride). Further, the polymer composition comprises a plasticizer (for example water). A sufficient amount of water is added the polymer composition such that the polymer composition exhibits a Capillary Number of at least 1.

A polymer composition of the present invention may be prepared using a screw extruder, such as a vented twin screw extruder.

A barrel 10 of an APV Baker (Peterborough, England) twin screw extruder is schematically illustrated in FIG. 1A. The barrel 10 is separated into eight zones, identified as zones 1-8. The barrel 10 encloses the extrusion screw and mixing elements, schematically shown in FIG. 1B, and serves as a containment vessel during the extrusion process. A solid feed port 12 is disposed in zone 1 and a liquid feed port 14 is disposed in zone 1. A vent 16 is included in zone 7 for cooling and decreasing the liquid, such as water, content of the mixture prior to exiting the extruder. An optional vent stuffer, commercially available from APV Baker, can be employed to prevent the polymer composition from exiting through the vent 16. The flow of the polymer composition through the barrel 10 is from zone 1 exiting the barrel 10 at zone 8.

Figure 1B:
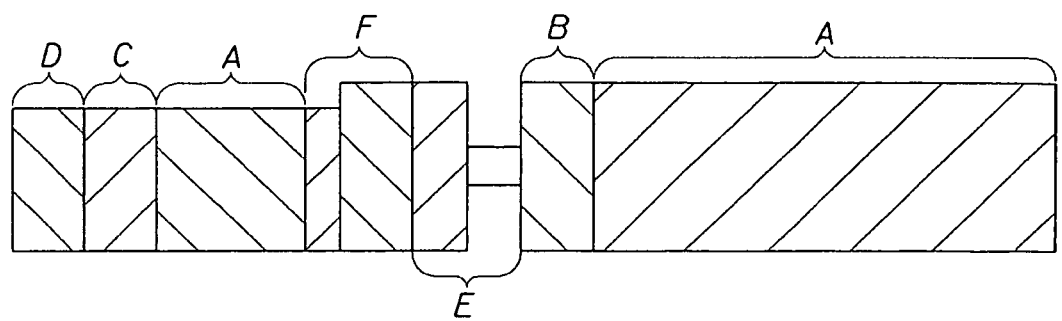
FIG. 1B is a schematic side view of a screw and mixing element configuration suitable for use in the barrel of FIG. 1A.

A screw and mixing element configuration for the twin screw extruder is schematically illustrated in FIG. 1B. The twin screw extruder comprises a plurality of twin lead screws (TLS) (designated A and B) and single lead screws (SLS) (designated C and D) installed in series. Screw elements (A-D) are characterized by the number of continuous leads and the pitch of these leads.

A lead is a flight (at a given helix angle) that wraps the core of the screw element. The number of leads indicates the number of flights wrapping the core at any given location along the length of the screw. Increasing the number of leads reduces the volumetric capacity of the screw and increases the pressure generating capability of the screw.

The pitch of the screw is the distance needed for a flight to complete one revolution of the core. It is expressed as the number of screw element diameters per one complete revolution of a flight. Decreasing the pitch of the screw increases the pressure generated by the screw and decreases the volumetric capacity of the screw.

The length of a screw element is reported as the ratio of length of the element divided by the diameter of the element.

This example uses TLS and SLS. Screw element A is a TLS with a 1.0 pitch and a 1.5 length ratio. Screw element B is a TLS with a 1.0 pitch and a 1.0 L/D ratio. Screw element C is a SLS with a ¼ pitch and a 1.0 length ratio. Screw element D is a SLS and a ¼ pitch and a ½ length ratio.

Bilobal paddles, E, serving as mixing elements, are also included in series with the SLS and TLS screw elements in order to enhance mixing. Various configurations of bilobal paddles and reversing elements F, single and twin lead screws threaded in the opposite direction, are used in order to control flow and corresponding mixing time.

In zone 1, a first hydroxyl polymer (for example dent corn starch) and/or first hydroxyl polymer composition (for example dent corn starch and an ethoxylated starch) is fed into the solid feed port at a rate of 183 grams/minute using a K-Tron (Pitman, N.J.) loss-in-weight feeder. A second hydroxyl polymer and/or second hydroxyl polymer composition is fed into the same port via a second K-tron feeder at a rate of 38 grams/minute.

Optionally the second hydroxyl polymer and/or second hydroxyl polymer composition may be prepared separately and added as a water-based polymer composition according to the following procedure. The second hydroxyl polymer and/or second hydroxyl polymer composition is prepared in a scraped wall reaction vessel (Chemplant Stainless Holdings Ltd. Dalton, England). The reaction vessel is capable of heating through an oil jacket and may be pressurized to prevent water loss at elevated temperatures. Water, an external plasticizer, is introduced into the vessel and while stirring the second hydroxyl polymer (for example polyvinyl alcohol) is added, optionally another hydroxyl polymer (for example an ethoxylated starch) may also be added during this step. Additional components such as surfactants or alkaline materials such as sodium/ammonium hydroxide may be added. The additive port of the reaction vessel is then closed, sealed and pressurized to 20 psi. The reaction vessel is then heated to about 110° C. while stirring for approximately one hour and then is pressure fed through supply lines to a B9000 pump for metered feeding into the zone 1 of the extruder, as previously described. Adjustments are made to the feed rates to keep the total polymer addition to about 220 grams/minute and the water to about 136 grams/minute.

The first hydroxyl polymer and/or first hydroxyl polymer composition and the second hydroxyl polymer and/or second hydroxyl polymer composition are combined inside the extruder (zone 1) with the water, an external plasticizer, added at the liquid feed at a rate of 136 grams/minute using a Milton Roy (Ivyland, Pa.) diaphragm pump (1.9 gallon per hour pump head) to form a third hydroxyl polymer composition. The third hydroxyl polymer composition is then conveyed down the barrel of the extruder and cooked, in the presence of an alkaline agent, such as ammonium hydroxide and/or sodium hydroxide. (introduction of external plasticizer such as glycerin) The cooking causes a hydrogen from at least one hydroxyl moiety on one or more of the hydroxyl polymers to become disassociated from the oxygen atom of the hydroxyl moiety and thus creates a negative charge on the oxygen atom of the former hydroxyl moiety. This oxygen atom is now open for substitution by a substitution agent, such as a cationic agent, such as a quaternary ammonium compound, for example a quaternary amine.

Table 1 describes the temperature, pressure, and corresponding function of each zone of the extruder.

TABLE 1

| Zone | Temp. (° F.) | Pressure | Description of Screw | Purpose |
|---|---|---|---|---|
| 1 | 70 | Low | Feeding/Conveying | Feeding and Mixing |
| 2 | 70 | Low | Conveying | Mixing and Conveying |
| 3 | 70 | Low | Conveying | Mixing and Conveying |
| 4 | 130 | Low | Pressure/Decreased Conveying | Conveying and Heating |
| 5 | 300 | Medium | Pressure Generating | Cooking at Pressure and Temperature |
| 6 | 250 | High | Reversing | Cooking at Pressure and Temperature |
| 7 | 210 | Low | Conveying | Cooling and Conveying (with venting) |
| 8 | 210 | Low | Pressure Generating | Conveying |

After the third hydroxyl polymer composition exits the extruder, part of the polymer composition can be dumped and another part (100 g) can be fed into a Zenith®, type PEP II (Sanford N C) and pumped into a SMX style static mixer (Koch-Glitsch, Woodridge, Ill.). The static mixer is used to combine additional additives such as crosslinking agents, crosslinking facilitators, external plasticizers, such as water, with the third hydroxyl polymer composition. The additives are pumped into the static mixer via PREP 100 HPLC pumps (Chrom Tech, Apple Valley Minn.). These pumps provide high pressure, low volume addition capability. The third hydroxyl polymer composition of the present invention exhibits a Capillary Number of at least 1 and thus, is ready to be polymer processed into a hydroxyl polymer fiber.

b. Polymer Processing the Polymer Composition into a Hydroxyl Polymer Fiber

The hydroxyl polymer composition is then polymer processed into a hydroxyl polymer fiber. Nonlimiting examples of polymer processing operations include extrusion, molding and/or fiber spinning. Extrusion and molding (either casting or blown), typically produce films, sheets and various profile extrusions. Molding may include injection molding, blown molding and/or compression molding. Fiber spinning may include spun bonding, melt blowing, continuous fiber producing and/or tow fiber producing. Fiber spinning may be dry spinning or wet spinning. Monocomponent fibers comprising the hydroxyl polymer composition are formed by the fiber spinning.

c. Forming Hydroxyl Polymer Fiber Fibrous Structure

Hydroxyl polymer fibers produced as a result of polymer processing of the polymer composition in accordance with the present invention may be combined into a fibrous structure by collecting a plurality of the fibers onto a belt or fabric.

A plurality of solid additives may be combined with the hydroxyl polymer fibers as the fibers are being deposited onto a collection device, such as a belt or fabric.

In one example, a first gas stream may comprise a plurality of hydroxyl polymer fibers and a second gas stream may comprise a plurality of solid additives. The two gas streams may be combined prior to and/or concurrently with depositing the hydroxyl polymer fibers and solid additives onto a collection device such that the solid additives are entrained within and/or on the resulting fibrous structure. An example of equipment suitable for use in this type of process are described in U.S. Patent Application 2003/0114067.

A fibrous structure of the present invention may then be post-processed by subjecting the web to a post-processing operation. Nonlimiting examples of post processing operations include contacting the fibrous structure with a plurality of solid additives, curing, embossing, thermal bonding, humidifying, perfing, calendering, printing, differential densifying, tuft deformation generation, and other known post-processing operations.

d. Contacting Surfaces of a Fibrous Structure with Solid Additives

Solid additives may be applied to a fibrous structure by any suitable means known in the art. When solid additives are applied to a fibrous structure, a surface of the fibrous structure comprising the solid additives is formed. A nonlimiting example by which solid additives may be applied to the fibrous structure is by using a Dan Web former, an example of which is described in U.S. Pat. No. 5,885,516, commercially available from Dan-Web of Risskov, Denmark.

Hydroxyl Polymer Fiber Fibrous Structure

Figure 2:
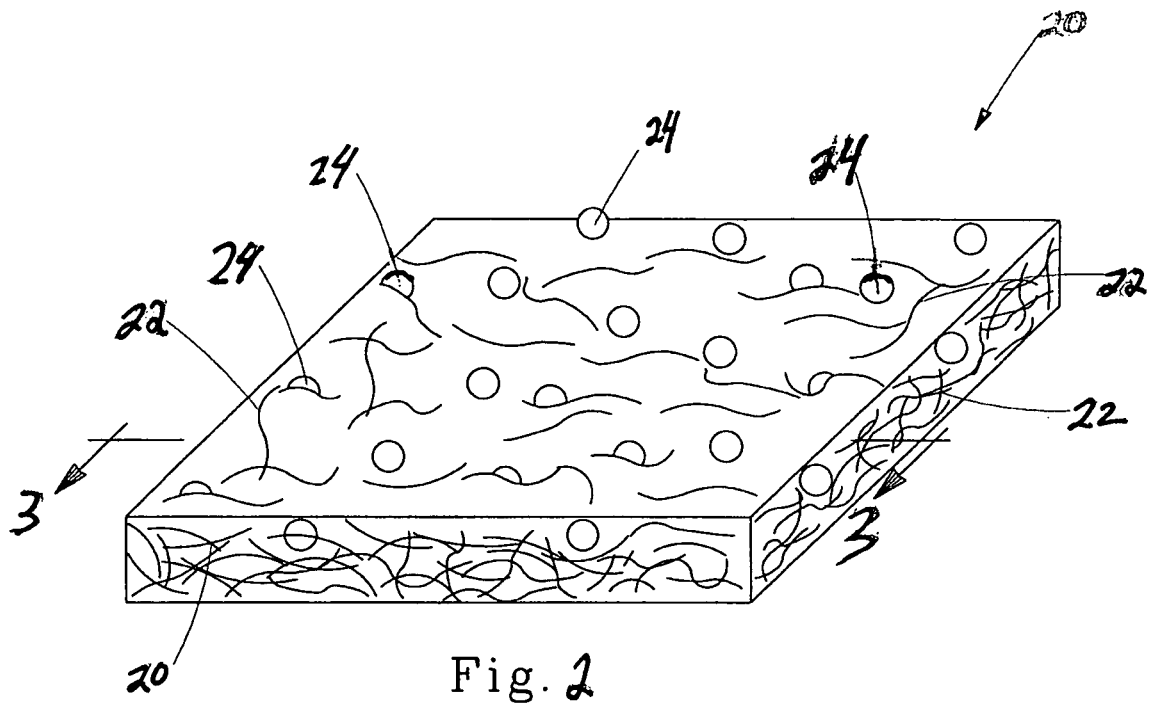
FIG. 2 is a schematic perspective representation of one example of a fibrous structure according to the present invention.

As shown in FIG. 2, a hydroxyl polymer fiber fibrous structure 20 comprises a hydroxyl polymer fiber 22 (a plurality of hydroxyl polymer fibers 22 may form a base substrate upon which solid additives may be deposited) and a solid additive 24, which may be a particle and/or a naturally occurring fiber.

Figure 3:
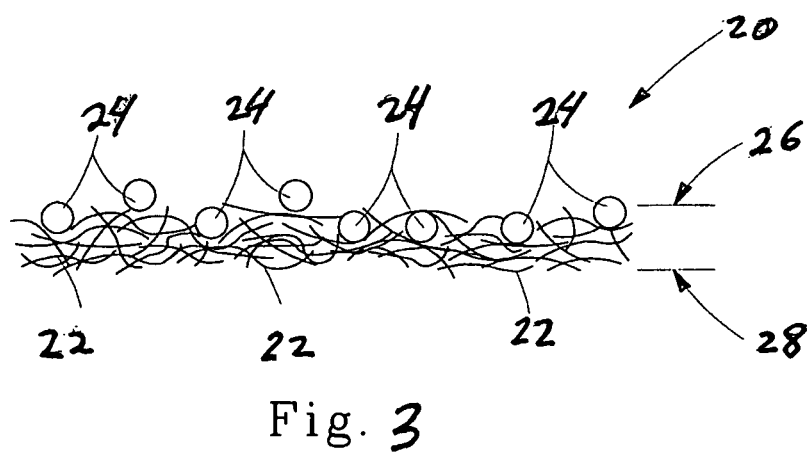
FIG. 3 is a cross-sectional view of the fibrous structure of FIG. 2 taken along line 3-3.

The hydroxyl polymer fiber fibrous structure 20 may comprise a first surface 26 and a second surface 28 opposite from the first surface 26 as shown in FIG. 3. The solid additive 24 may be present on a surface of the fibrous structure, such as the first surface 26. The solid additive 24 may cover less than the entire surface area of the surface of the fibrous structure. The solid additive 24 may be present on the surface of the fibrous structure in a random pattern. The solid additive 24 may be present on the surface of the fibrous structure in a non-random repeating pattern.

For explanation and/or clarity purposes, the solid additives 24 are shown in a dispersed nature, however, the concentration of the solid additives 24 on the first surface 26 of the hydroxyl polymer fiber fibrous structure 20 and/or the second surface 28 of the hydroxyl polymer fiber fibrous structure 20 may be such that the entire surface area or almost the entire surface area of the first surface 26 and/or the second surface 28 may be in contact with the solid additives 24.

Figure 4:
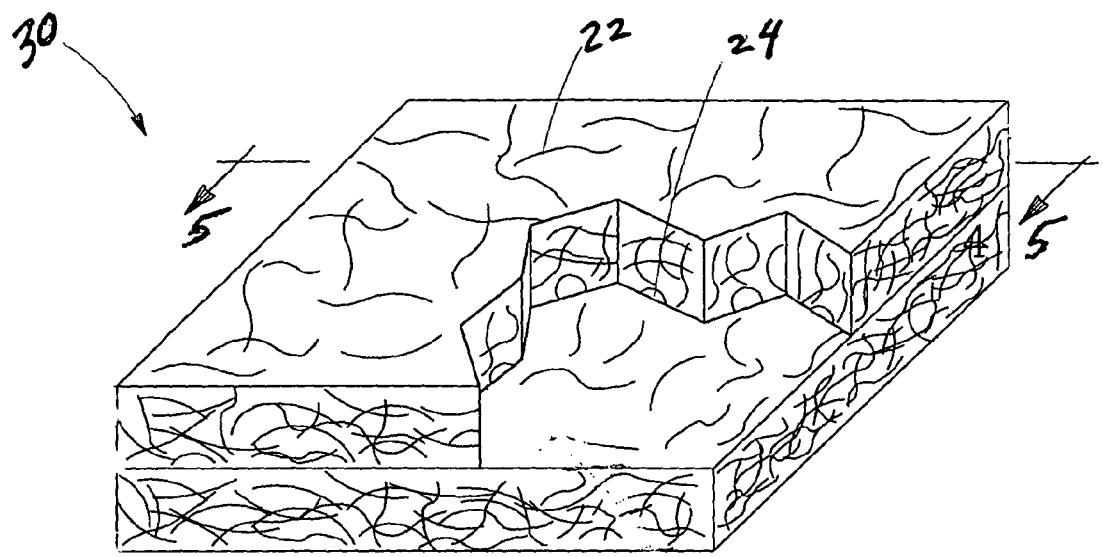
FIG. 4 is a schematic perspective representation of one example of a multi-layered fibrous structure according to the present invention with a partial cut-away to expose the layers.
Figure 5:
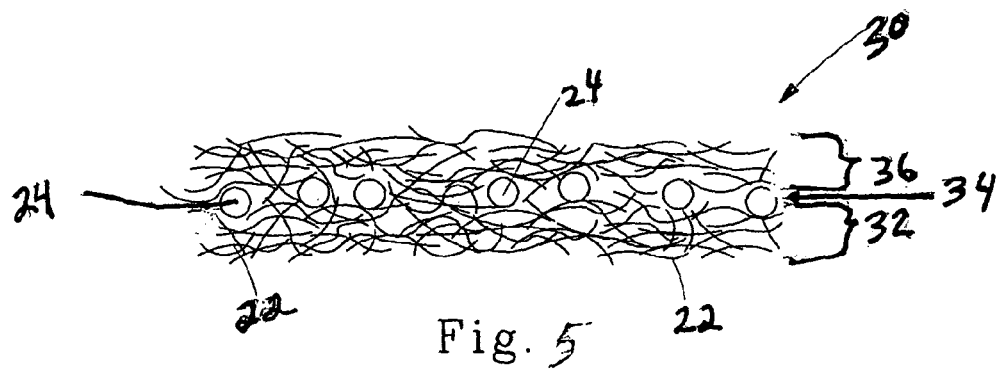
FIG. 5 is a cross-sectional view of the multi-layered fibrous structure of FIG. 4 taken along line 5-5.

As shown in FIGS. 4 and 5, in one example of the present invention, a multi-layered hydroxyl polymer fiber fibrous structure 30 comprises a first layer 32 comprising a plurality of hydroxyl polymer fibers, a second layer 34 comprising a plurality of solid additives, and a third layer 36 comprising a plurality of hydroxyl polymer fibers.

In one example, the fibrous structure 30 may comprise at least one layer comprising a majority of non-naturally occurring hydroxyl polymer fibers 22 and at least one layer comprising a majority of solid additives 24.

In another example, the solid additives 24 may be uniformly or substantially uniformly distributed throughout the fibrous structure.

In yet another example, the solid additives 24 may be non-uniformly distributed throughout the fibrous structure.

Figure 6:
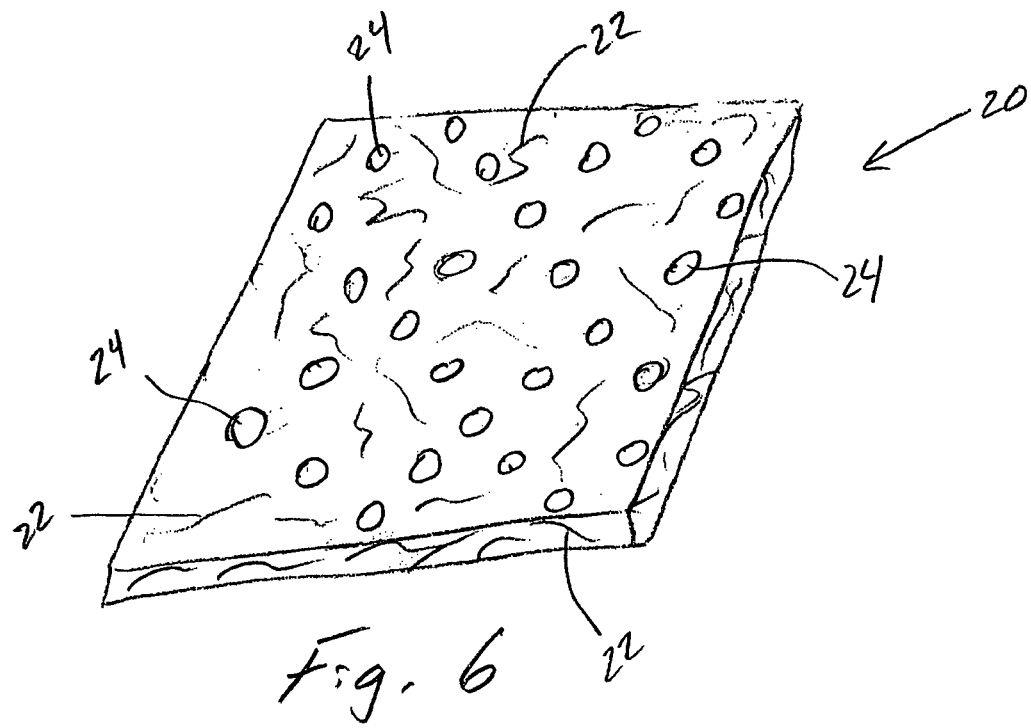
FIG. 6 is a schematic perspective representation of another example of a fibrous structure according to the present invention.

FIG. 6 illustrates still another example of a hydroxyl polymer fiber fibrous structure of the present invention. The hydroxyl polymer fiber fibrous structure 20 comprises a hydroxyl polymer fiber 22 and a plurality of solid additives 24. As shown in FIG. 6, the plurality of solid additives 24 are arranged in a non-random, repeating pattern on a surface of the hydroxyl polymer fiber fibrous structure 20. Depositing the solid additives in a non-random, repeating pattern can be achieved by any suitable means known in the art. For example, a patterned mask may be placed on the hydroxyl polymer fiber fibrous structure such that only the open areas of the mask allow the solid additives to contact a surface of the hydroxyl polymer fiber fibrous structure.

Figure 7:
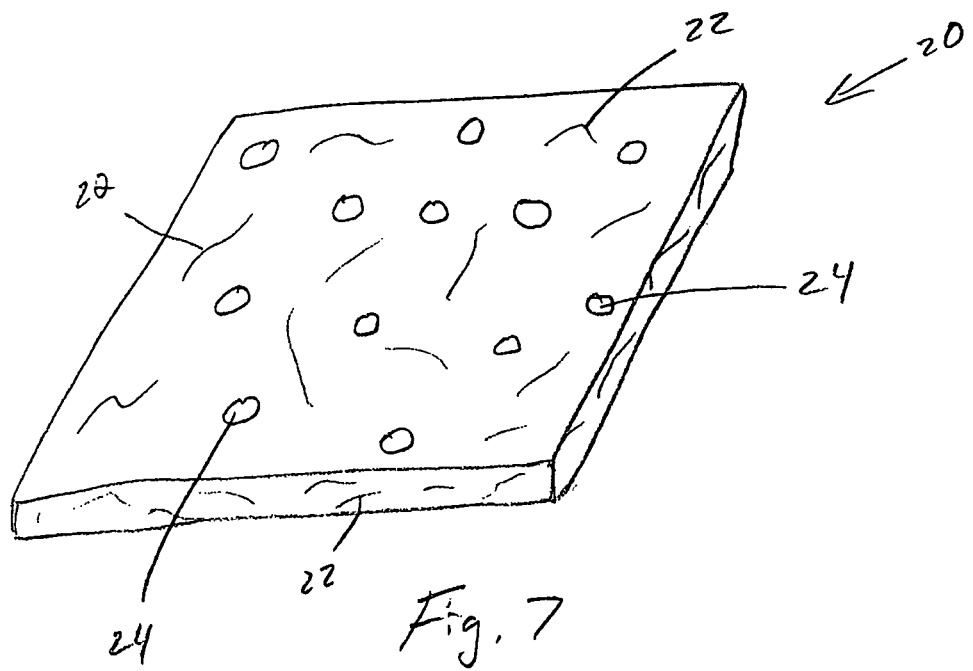
FIG. 7 is a schematic perspective representation of another example of a fibrous structure according to the present invention.

FIG. 7 illustrates still yet another example of a hydroxyl polymer fiber fibrous structure of the present invention. The hydroxyl polymer fiber fibrous structure 20 comprises a hydroxyl polymer fiber 22 and a plurality of solid additives 24. As shown in FIG. 7, the plurality of solid additives 24 are arranged in a random pattern on a surface of the hydroxyl polymer fiber fibrous structure 20.

In one example, the hydroxyl polymer fiber fibrous structure of the present invention may comprise greater than 40% and/or greater than 45% and/or greater than 50% by bone dry weight of the hydroxyl polymer fibers.

In another example, the hydroxyl polymer fiber fibrous structure of the present invention may comprise less than 60% and/or less than 50% and/or less than 30% and/or less than 15% and/or less than 5% and/or less than 2% by bone dry weight of the solid additives.

Test Methods

Unless otherwise indicated, all tests described herein including those described under the Definitions section and the following test methods are conducted on samples that have been conditioned in a conditioned room at a temperature of 73° F.±4° F. (about 23° C.±2.2° C.) and a relative humidity of 50%±10% for 24 hours prior to the test. Samples conditioned as described herein are considered dry samples (such as "dry fibrous structures") for purposes of this invention. Further, all tests are conducted in such conditioned room.

Tested samples and felts should be subjected to 73° F.±4° F. (about 23° C.±2.2° C.) and a relative humidity of 50%±10% for 24 hours prior to testing.

A. Pore Volume Distribution Test Method

Pore Volume Distribution measurements are made on a TRI/Autoporosimeter (TRI/Princeton Inc. of Princeton, N.J.). The TRI/Autoporosimeter is an automated computer-controlled instrument for measuring pore volume distributions in porous materials (e.g., the volumes of different size pores within the range from 1 to 900 µm effective pore radii). Complimentary Automated Instrument Software, Release 2000.1, and Data Treatment Software, Release 2000.1 is used to capture, analyze and output the data. More information on the TRI/Autoporosimeter, its operation and data treatments can be found in The Journal of Colloid and Interface Science 162 (1994), pgs 163-170, incorporated here by reference.

As used in this application, determining Pore Volume Distribution involves recording the increment of liquid that enters or leaves a porous material as the surrounding air pressure changes. A sample in the test chamber is exposed to precisely controlled changes in air pressure. The size (radius) of the largest pore able to hold liquid is a function of the air pressure. As the air pressure increases (decreases), different size pore groups drain (absorb) liquid. The pore volume of each group is equal to this amount of liquid, as measured by the instrument at the corresponding pressure. The effective radius of a pore is related to the pressure differential by the following relationship.

$$\text{Pressure differential}=[(2)\gamma \cos \Theta)]/\text{effective radius}$$

where $\gamma$=liquid surface tension, and $\Theta$=contact angle.

Typically pores are thought of in terms such as voids, holes or conduits in a porous material. It is important to note that this method uses the above equation to calculate effective pore radii based on the constants and equipment controlled pressures. The above equation assumes uniform cylindrical pores. Usually, the pores in natural and manufactured porous materials are not perfectly cylindrical, nor all uniform. Therefore, the effective radii reported here may not equate exactly to measurements of void dimensions obtained by other methods such as microscopy. However, these measurements do provide an accepted means to characterize relative differences in void structure between materials.

The equipment operates by changing the test chamber air pressure in user-specified increments, either by decreasing pressure (increasing pore size) to absorb liquid, or increasing pressure (decreasing pore size) to drain liquid. The liquid volume absorbed (drained) at each pressure increment is the cumulative volume for the group of all pores between the preceding pressure setting and the current setting.

In this application of the TRI/Autoporosimeter, the liquid is a 0.2 weight % solution of octylphenoxy polyethoxy ethanol (Triton X-100 from Union Carbide Chemical and Plastics Co. of Danbury, Conn.) in distilled water. The instrument calculation constants are as follows: $\rho$ (density)=1 g/cm³; $\gamma$ (surface tension)=31 dynes/cm; cos $\Theta$=1. A 0.22 µm Millipore Glass Filter (Millipore Corporation of Bedford, Mass.; Catalog # GSWP09025) is employed on the test chamber's porous plate. A plexiglass plate weighing about 24 g (supplied with the instrument) is placed on the sample to ensure the sample rests flat on the Millipore Filter. No additional weight is placed on the sample. The remaining user specified inputs are described below. The sequence of pore sizes (pressures) for this application is as follows (effective pore radius in µm): 1, 2.5, 5, 10, 15, 20, 30, 40, 50, 60, 70, 80, 90, 100, 120, 140, 160, 180, 200, 225, 250, 275, 300, 350, 400, 450, 500, 600, 700, 800, 900, 800, 700, 600, 500, 450, 400, 350, 300, 275, 250, 225, 200, 180, 160, 140, 120, 100, 90, 80, 70, 60, 50, 40, 30, 20, 15, 10, 5, 2.5, 1, 2.5, 5, 10, 15, 20, 30, 40, 50, 60, 70, 80, 90, 100, 120, 140, 160, 180, 200, 225, 250, 275, 300, 350, 400, 450, 500, 600, 700, 800, 900. This sequence starts with the sample dry, saturates it as the pore settings increase ($1^{st}$ absorption), and then subsequently drains the sample of all volume above an effective pore radius of 1.0 µm (desorption), and then finally saturates it again as the pore settings increase a second time ($2^{nd}$ absorption). The equilibrium rate is set at 5 mg/minute. No stop radius is specified.

In addition to the test materials, a blank condition (no sample between plexiglass plate and Millipore Filter) is run to account for any surface and/or edge effects within the chamber. Any pore volume measured for this blank run is subtracted from the applicable pore grouping of the test sample. This data treatment can be accomplished manually or with the available TRI/Autoporosimeter Data Treatment Software, Release 2000.1.

In regards to wet fibrous structure (web) collapse, the characteristic pore size distribution of the $2^{nd}$ absorption portion of the testing sequence is analyzed, since absorption in the $1^{st}$ absorption portion of the testing sequence can sometimes vary based on how the dry fibrous structure contacts the wetted filter (influenced by dry fibrous structure texture, embossing, etc.). Thus, after the desorption portion of the testing sequence, the sample, already wetted once, is expected to be in better hydraulic contact with the porous filter (due to lower fiber and fibrous structure (web) modulus when wet).

The TRI/Autoporosimeter reports the weight (mg) of liquid absorbed/desorbed from each pore group as chamber pressure is step changed according to the prescribed testing sequence. From this data, the liquid density, and the weight of the original, dry sample, the ratio of pore volume/sample weight can be calculated. This value can be reported as mm³/mg of dry sample mass. Similarly, the pore volume/dry sample weight over a specified pore size range (e.g., 20-500 µm) can be calculated by simply summing the reported pore volumes of each pore setting included in that range and dividing by the dry sample mass. These data treatments are conducted manually based on the output of the Automated Instrument Software, Release 2000.1.

B. Fiber Diameter Test Method

A fibrous structure comprising hydroxyl polymer fibers of appropriate basis weight (approximately 5 to 20 grams/square meter) is cut into a rectangular shape, approximately 20 mm by 35 mm. The sample is then coated using a SEM sputter coater (EMS Inc, PA, USA) with gold so as to make the fibers relatively opaque. Typical coating thickness is between 50 and 250 nm. The sample is then mounted between two standard microscope slides and compressed together using small binder clips. The sample is imaged using a 10× objective on an Olympus BHS microscope with the microscope light-collimating lens moved as far from the objective lens as possible. Images are captured using a Nikon D1 digital camera. A Glass microscope micrometer is used to calibrate the spatial distances of the images. The approximate resolution of the images is 1 µm/pixel. Images will typically show a distinct bimodal distribution in the intensity histogram corresponding to the fibers and the background. Camera adjustments or different basis weights are used to achieve an acceptable bimodal distribution. Typically 10 images per sample are taken and the image analysis results averaged.

The images are analyzed in a similar manner to that described by B. Pourdeyhimi, R. and R. Dent in "Measuring fiber diameter distribution in nonwovens" (Textile Res. J. 69(4) 233-236, 1999). Digital images are analyzed by computer using the MATLAB (Version. 6.3) and the MATLAB Image Processing Tool Box (Version 3.) The image is first converted into a grayscale. The image is then binarized into black and white pixels using a threshold value that minimizes the intraclass variance of the thresholded black and white pixels. Once the image has been binarized, the image is skeletonized to locate the center of each fiber in the image. The distance transform of the binarized image is also computed. The scalar product of the skeltonized image and the distance map provides an image whose pixel intensity is either zero or the radius of the fiber at that location. Pixels within one radius of the junction between two overlapping fibers are not counted if the distance they represent is smaller than the radius of the junction. The remaining pixels are then used to compute a length-weighted histogram of fiber diameters contained in the image.

All documents cited in the Detailed Description of the Invention are, in relevant part, incorporated herein by reference; the citation of any document is not to be construed as an admission that it is prior art with respect to the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments/examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A spun, thermally bonded fibrous structure comprising a plurality of spun, monocomponent, non-naturally occurring polysaccharide fibers comprising a crosslinked polysaccharide selected from the group consisting of: starch, starch derivatives, and mixtures thereof, wherein the polysaccharide fibers exhibit a length of greater than 3.81 cm and one or more of the polysaccharide fibers exhibits a fiber diameter of less than 10 microns as determined by the Fiber Diameter Test Method described herein, and a plurality of solid additives comprising naturally occurring fibers that are entrained within the fibrous structure.

2. The fibrous structure according to claim 1 wherein the fibrous structure exhibits a total pore volume of greater than 3.75 mm$^3$/mg of dry fibrous structure mass for pores with an effective pore radius in the range of 20 μm to 500 μm.

3. The fibrous structure according to claim 1 wherein the fibrous structure further comprises solid additives that are present on at least one surface of the fibrous structure.

4. The fibrous structure according to claim 3 wherein the solid additives cover less than the entire surface area of the surface of the fibrous structure.

5. The fibrous structure according to claim 3 wherein the solid additives are present on the surface of the fibrous structure in a non-random repeating pattern.

6. The fibrous structure according to claim 1 wherein the solid additives are non-uniformly distributed throughout the fibrous structure.

7. The fibrous structure according to claim 1 wherein at least one of the solid additives exhibits a critical surface tension of greater than about 30 dynes/cm.

8. The fibrous structure according to claim 1 wherein the solid additives further comprise a solid additive selected from the group consisting of: hydrophilic inorganic particles, hydrophilic organic particles, hydrophobic inorganic particles, hydrophobic organic particles, non-naturally occurring particles, other non-naturally occurring fibers, and mixtures thereof.

9. The fibrous structure according to claim 1 wherein the naturally occurring fibers comprise a wood pulp fiber.

10. The fibrous structure according to claim 1 wherein the naturally occurring fibers comprise a cotton linter.

11. The fibrous structure according to claim 1 wherein the naturally occurring fibers comprise protein.

12. The fibrous structure according to claim 1 wherein the fibrous structure comprises at least one layer comprising a majority of non-naturally occurring polysaccharide fibers and at least one layer comprising a majority of solid additives.

13. The fibrous structure according to claim 1 wherein at least one of the spun, monocomponent, non-naturally occurring polysaccharide fibers further comprises a hydroxyl polymer selected from the group consisting of: polyvinyl alcohol, polyvinyl alcohol derivatives, polyvinyl alcohol copolymers, proteins, and mixtures thereof.

14. The fibrous structure according to claim 1 wherein at least one of the solid additives exhibits a particle size of less than 6 mm in the maximum dimension.

15. The fibrous structure according to claim 1 wherein the fibrous structure comprises less than 50% by bone dry weight of the solid additives.

16. A spun, thermally bonded fibrous structure comprising a plurality of spun, monocomponent, non-naturally occurring hydroxyl polymer fibers that exhibit a length of greater than 3.81 cm and one or more of the spun, non-naturally occurring hydroxyl polymer fibers exhibits a fiber diameter of less than 10 microns as determined by the Fiber Diameter Test Method described herein, and solid additives comprising naturally occurring fibers that are entrained within the fibrous structure, wherein the spun, non-naturally occurring hydroxyl polymer fibers comprise a crosslinked polysaccharide selected from the group consisting of: starch, starch derivatives, and mixtures thereof, are present at a greater bone dry weight than the solid additives wherein the fibrous structure exhibits a total pore volume of greater than 3.75 mm$^3$/mg of dry fibrous structure mass for pores with an effective pore radius in the range of 20 μm to 500 μm.

17. A spun, thermally bonded fibrous structure comprising a plurality of spun, monocomponent, non-naturally occurring hydroxyl polymer fibers that exhibit a length of greater than 3.81 cm and one or more of the spun, non-naturally occurring hydroxyl polymer fibers exhibits a fiber diameter of less than 10 microns as determined by the Fiber Diameter Test Method described herein, wherein the spun, non-naturally occurring hydroxyl polymer fibers comprise a crosslinked polysaccharide selected from the group consisting of: starch, starch derivatives, and mixtures thereof, and a pore volume enhancing system that increases the total pore volume of the fibrous structure for pores with an effective pore radius in the range of 20 μm to 500 μm compared to the total pore volume for pores with an effective pore radius in the range of 20 μm to 500 μm of the same fibrous structure without the pore volume enhancing system, wherein the pore volume enhancing system comprises naturally occurring fibers that are entrained within the fibrous structure.

18. The fibrous structure according to claim 17 wherein the fibrous structure exhibits a total pore volume of greater than 3.75 mm$^3$/mg of dry fibrous structure mass for pores with an effective pore radius in the range of 20 μm to 500 μm.

* * * * *